United States Patent [19]

Kukolja et al.

[11] 3,960,844

[45] June 1, 1976

[54] PREPARATION OF 6-ACYLAMINO-2-METHYL-2-HALOMETHYL PENAMS

[75] Inventors: Stjepan Kukolja, Indianapolis; Steven R. Lammert, Greenwood, both of Ind.

[73] Assignee: Eli Lilly and Company, Indianapolis, Ind.

[22] Filed: Feb. 11, 1975

[21] Appl. No.: 548,953

Related U.S. Application Data

[63] Continuation-in-part of Ser. No. 465,778, May 1, 1974, abandoned.

[52] U.S. Cl. ........................ 260/239.1; 260/243 C
[51] Int. Cl.² ........................................ C07C 499/44
[58] Field of Search ..................... 260/239.1, 243 C

[56] References Cited

OTHER PUBLICATIONS

Kukolja et al, J.A.C.S., vol. 94, pp. 7169–7170, (1972).

*Primary Examiner*—Gerald A. Schwartz
*Attorney, Agent, or Firm*—Steven R. Lammert; Everet F. Smith

[57] ABSTRACT

A 7-acylamino-3-hydroxy-3-methylcepham-4-carboxylic acid ester is reacted with a mixture of a halogenating agent and a tertiary carboxamide to produce a 2-halomethylpenam compound, a useful intermediate for the preparation of desacetoxycephalosporins.

13 Claims, No Drawings

PREPARATION OF 6-ACYLAMINO-2-METHYL-2-HALOMETHYL PENAMS

CROSS-REFERENCE TO RELATED APPLICATION

This application is a continuation-in-part of our co-pending U.S. application Ser. No. 465,778, filed May 1, 1974 now abandoned.

BACKGROUND OF THE INVENTION

Cephalosporin antibiotics have recently achieved considerable success in the treatment of infectious diseases of man. This particular class of antibiotics has been prepared by two known general procedures. In the first of these methods, cephalosporin C is produced by culturing the organism *Cephalosporium acremonium*, Newton and Abraham, *Biochem. J.*, 62, 651 (1956). Cleavage of the cephalosporin C 2-aminoadipoyl side chain according to the method described in U.S. Pat. No. 3,188,311 affords 7-aminocephalosporanic acid (7-ACA). Acylation of 7-ACA with an appropriate acid halide or mixed anhydride yields the expected 7-acylaminocephaloporanic acid. The cephalosporin antibiotics obtained from cephalosporin C according to this method are derivatives of cephalosporanic acid which are substituted at the 3-position of the cephalosporin nucleus with an acetoxymethyl group. According to the cephem nomenclature system for cephalosporins, the cephalosporin antibiotics obtained from cephalosporin C are named 7-acylamido-3-acetoxymethyl-3-cephem-4-carboxylic acids.

The second method by which the cephalosporin antibiotics are prepared involves the ring expansion of the thiazolidine ring of a penicillin. In this procedure, described in U.S. Pat. No. 3,275,626, the fused B-lactam ring of the penicillin molecule remains intact. This chemical conversion is carried out by heating a penicillin sulfoxide compound in the presence of an acidic reagent, such as acetic anhydride, to obtain predominantly a 7-acylamino-3-methyl-3-cephem-4-carboxylic acid ester (a desacetoxycephalosporin) and a 7-acylamino-3-methyl-3-acyloxycepham-4-carboxylic acid ester. Also produced in this chemical conversion is a 2-acyloxymethylpenicillin, otherwise designated as a 6-acylamino-2-methyl-2-acyloxymethylpenam-3-carboxylic acid ester.

U.S. Pat. No. 3,275,626 additionally discusses the possibility of converting a penicillin sulfoxide by heating it in the presence of any one of various acidic reagents. The ultimate relative proportions of the products resulting from such reactions depend to some extent upon the particular acid which is employed, with the substituents present in the acid, as well as the particular structure and relative strength of the acid having some effect on the product mix formed.

produced: carrying out the reaction of a penicillin sulfoxide ester with thionyl chloride, it has been found that the following products are among those produced:

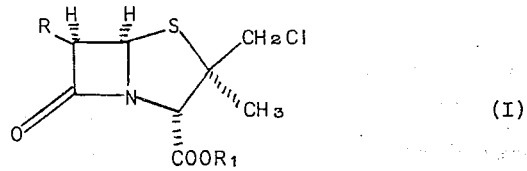

(I)

and

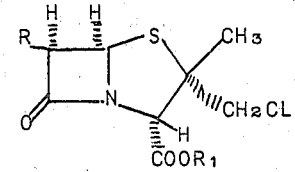

(II)

and

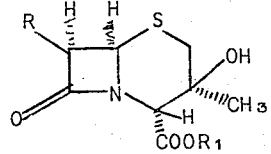

(III)

It further has been found that a 2α-methyl-2β-halomethyl penam (I) is unstable and gradually rearranges to the corresponding 3β-halo-3α-methylcepham of the formula

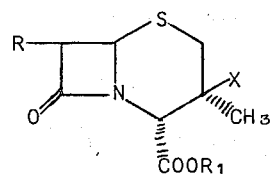

IV

[See, e.g., Netherlands Pat. No. 7,208,671.] This rearrangement occurs spontaneously at room temperature over a period of time ranging from several days to several months depending on the particular compound and the conditions to which it is subjected. The rearrangement can be greatly accelerated by subjecting the penam to an elevated temperature, for example, from about 50°C. to about 100°C., under which conditions, the rearrangement can be accomplished in as little as one hour. Conversion to the corresponding 3α-methyl-3β-halocepham can also be effected by maintaining the unstable penam in a suitable inert solvent on a chromatographic column for a period of from about 24 to about 72 hours and then eluting the cepham product from the column.

Generally, the 2β-bromomethyl penam compounds undergo such a rearrangement more rapidly than the corresponding 2β-chloromethylpenam compounds.

It has been shown that a 6-imido-2-methyl-2-chloromethylpenam-3-carboxylic acid ester can be prepared from the corresponding 3-hydroxy-3-metyl-cepham such as designated by Formula III, by reacting said 3-hydroxy compound with thionyl chloride in the presence of triethylamine at elevated temperatures [S. Kukolja and S. R. Lammert, *J. Amer. Chem. Soc.*, 94, 7169 (1972) ]. Attempts at preparing 6-acylamino-2-methyl-2-halomethylpenam-3-carboxylic acid esters from the related 3-hydroxy substituted cepham compounds under similar reaction conditions resulted in recovery of starting materials. Thus, the 6-acylamino-2-methyl-2-halomethylpenam-3-carboxylic acid esters have been inaccessible through previously described procedures which have been successfully applied to the preparation of the corresponding 6-imido-2-methyl-2-halomethylpenam compounds.

Briefly, in accordance with this invention, it has now been discovered that it is possible to convert a 7-acylamino-3-hydroxy-3-methylcepham-4-carboxylic acid ester having the structure depicted by Formula III (R=RCONH—) to a 6-acylamino-2α-methyl-2β-halomethylpenam-3-carboxylic acid ester (I), an intermediate useful in the preparation of active desacetoxycephalosporin antibiotics.

SUMMARY OF THE INVENTION

The present invention is directed to a process for converting a cepham compound, which comprises reacting a compound of the formula

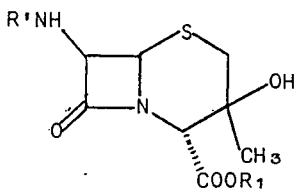

with a mixture of a halogenating agent of the formula $CO(X)_2$, $P(X)_5$, $SO(X)_2$ and a tertiary carboxamide to obtain a compound of the formula

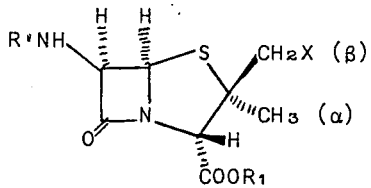

in which, in the above formulae, R' is an acyl group, $R_1$ is a carboxy protecting group, and X is chlorine or bromine.

DETAILED DESCRIPTION OF THE INVENTION

The process of this invention is carried out by reacting a 7-acylamino-3-hydroxy-3-methylcepham-4-carboxylic acid ester with a halogenating agent selected from the group consisting of phosphorous pentachloride, phosphorous pentabromide, thionyl chloride, thionyl bromide, carbonyl chloride (phosgene), and carbonyl bromide in the presence of a tertiary carboxamide. Preferred halogenating agents are thionyl chloride and phosphorous pentachloride.

The reaction is carried out at a temperature of about 50° to about 120°C. More preferably, the reaction temperature is between 60° and 90°C. Typically, the time of the reaction will range from 10 minutes to about 1 hour with the reaction time being to some extent dependent upon the particular reactants, the solvents employed, and the temperature at which the reaction is carried out. Normally, the higher the temperature of the reaction, the shorter the reaction time required for its completion. Usually, the reaction will be completed after the reactants have been maintained in contact at preferred temperatures for about 20 to 40 minutes.

The conversion substantially 7-acylamino-3 -hydroxy-3-methylcepham compounds to the corresponding 2β-halomethylpenam derivatives is preferably, though not necessarily, carried out in a substantially anhydrous aprotic solvent, specifically, one which facilitates the dissolution, and thus, adequate mixing of the reactants. A substantialy anhydrous aprotic solvent, within the scope of this specification, refers to a type of solvent which does not offer or accept protons but which might possibly still contain trace amounts of water. It is well known by those skilled in the art that water hydrolyzes halogenating agents such as those named hereinabove. Therefore, the amount of moisture in contact with the reagents should be minimized. Trace amounts of water such as that found in commercially dried solvents, can be tolerated but should be considered when determining the amount of halogenating agent to be used; thus a slight excess of the halogenating agent over and above the amount that would be employed under strictly anhydrous conditions might be needed for the completion of the halogenation process of this invention. Suitable solvents are those having a boiling point at least as high as the temperature required for the reaction and include, for example, aromatic hydrocarbons, such as benzene, toluene, and the like; halogenated hydrocarbons, such as carbon tetrachloride, chlorobenzene, bromobenzene, bromoform, chloroform, 1,2-dichloroethane, 1,2-dibromoethane, and the like; aliphatic nitriles, such as acetonitrile, propionitrile, and the like; esters, such as ethyl acetate, butyl acetate, and the like; ethers, such as dioxane, 1,2-dimethoxyethane, and the like; tertiary carboxamides, such as N,N-dimethylformide, N,N-dimethylacetamide, and the like; and any other appropriate aprotic solvent. Preferred solvents are those having a boiling point with the temperature range at which the reaction is to be carried out, thereby permitting the reaction mixture to be refluxed while retaining temperature control. However, for solvents not in this category, the temperature can be easily controlled by conventional means. Highly preferred solvents for the process of this invention include benzene, toluene, and the tertiary amides such as N,N-dimethylacetamide, N-methyl-2-pyrrolidinone and N,N-dimethylformamide and mixtures thereof.

Because of the moisture sensitivity of the halogenating agents employed in this process, the use of substantially anhydrous solvents is required as stated above. Furthermore, care must also be taken to exclude moisture from the reaction mixture during the course of the reaction. The maintenance of anhydrous conditions can be accomplished by any one of a number of techniques known to those skilled in the art.

The conversion of the 3-hydroxy-3-methylcepham is achieved in the presence of both the halogenating reagent and the tertiary carboxamide. The halogen reagent is selected from the group consisting of phosphorous pentachloride, thionyl chloride, carbonyl chloride (phosgene), phosphorous pentabromide thionyl bromide and carbonyl bromide. In order to ensure the presence of sufficient halogenating agent, preferably at least 1 molar equivalent of the halogenating agent is used per each mole of the 3-hydroxy-3-methylcepham. Usually a molar excess of the halogenating reagent will be employed, and typically the amount of halogenating reagent will range from slightly over equimolar to about 2.5 moles of the halogenating agent per mole of the 3-hydroxy-3-methylcepham compound. Preferably, the halogentating agent will be employed in an amount of from about 1.1 to about 2.0 moles per each mole of the 3-hydroxy-3 -methylcepham compound. In reference to previous statements within this description, the excess halogenating agent should eliminate any problems which might be incurred by the use of commercially dried solvents containing trace amounts of water.

The identity of the halo group present in the 2α-methyl-2β-chloromethylpenam compound which is formed in the herein described process of this invention is dependent on the identity of the halogen in the halogenating reagent. If the halogenating reagent is a chlorine compound the product will be a 2α-methyl-2β-chloromethylpenam compound. If the halogenating reagent is a bromine compound the product will be a 2α-methyl-2β-bromomethylpenam compound.

The other reactant which is employed in the conversion of the 7-acylamino-3-hydroxy-3-methylcepham-4-carboxylic acid ester is a tertiary carboxamide reagent. As stated hereinabove the tertiary carboxamide may be used as the solvent system, or it may be employed in conjunction with another aprotic solvent.

The general types of tertiary carboxamides which can be used have the structural formula.

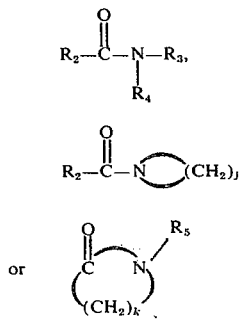

wherein $R_2$ is hydrogen, or $C_1-C_6$ alkyl and each of $R_3$ and $R_4$ is independently $C_1-C_6$ alkyl, phenyl, tolyl or xylyl, such that $R_3$ and $R_4$ together contain no more than about 11 carbon atoms; $R_5$ is $C_1-C_6$ alkyl, phenyl, tolyl, or xylyl; $j$ is an integer from 3 to 6 inclusive; and $k$ is an integer from 3 to 6 inclusive.

Examples of tertiary carboxamides of the types described above, which may be included in the process include: N,N-dimethylformamide, N,N-diethylformamide, N,N-dipentylformamide, N-methyl-N-ethylformamide, N-methyl-N-phenyl-formamide, N-ethyl-N-(m-tolyl) formamide, N,N-dimethylacetamide, N,N-diethylacetamide, N,N-diisopropylacetamide N,N-dibutylacetamide, N,N-dimethylbutamide, N-(3,5-dimethylphenyl)-N-methylpropionamide, and the like. Also included are the cyclic tertiary carboxamides: N-formylpiperidine, N-acetylpyrrolidine, N-propionyl-morpholine, N-butanoylpiperidine, N-methyl-2-pyrrolidone, N-butyl-2-piperidone, N-ethyl-2-piperidone, N-isopropyl-2-pyrrolidone, and the like. However, highly preferred tertiary carboxamides for the herein described process include N,N-dimethylformamide, N,N-dimethylacetamide and N-methyl-2-pyrrolidone.

The tertiary carboxamide which is employed should be present in an amount at least about equimolar to the amount of halogenating agent. Although typically a 1–20 molar excess of the tertiary carboxamide (with respect to the amount of halogenating agent) is employed when the process is carried out in an aprotic solvent other than a tertiary carboxamide, the amount of tertiary carboxamide can be increased to the extent that the tertiary carboxamide is utilized as the sole solvent for the reaction, provided of course, that the tertiary carboxamide used as said solvent exists in the liquid state at the temperatures required to promote the halogenation process. Thus, a wide range of solvent mixtures comprising various proportions of a tertiary carboxamide and another of the hereinabove described aprotic solvents are suitable in this process. Generally volume ratios of the tertiary carboxamide and the inert organic liquid range from about 1 part in 1,000 parts respectively to about 100% tertiary carboxamide. Preferably, however, the herein described process for conversion of a 7-acylamino-3-hydroxy-3-methylcepham is carried out either in an inert aprotic organic liquid, employing a 5–10 molar excess (with respect to the halogenating agent) of a tertiary carboxamide or in a tertiary carboxamide solvent.

As mentioned hereinabove, the 3-hydroxy-3-methyl-cepham compound used as starting material in the process of this invention can be prepared by reacting the corresponding penicillin sulfoxide with thionyl chloride in accordance with the general reaction described in U.S. Pat. No. 3,275,626. The 3-hydroxy-3-methylcepham compounds are also available in accordance with the techniques described in U.S. Pat. Nos. 3,668,201 and 3,668,202 (involving heating a penicillin sulfoxide in the presence of sulfuric or sulfamic acid) or by acylation of compounds described therein with an appropriate acid chloride reagent by techniques known to those skilled in the art. The 3-hydroxy-3-methylcepham used as starting material in the process of this invention has the following formula:

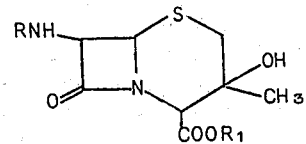

$R_1$ in the above formula as well as in the products of the process of this invention denotes a carboxy protecting group. The nature of the carboxy protecting group is not important and any of those known in the art and stable under the conditions of the process of this invention can be used. Preferably, however, this group is the residue of an ester function which is removable by known methods, such as, by the use of trifluoroacetic acid, acetic acid and zinc dust, dilute aqueous base or by hydrogenation in the presence of an appropriate catalyst such as palladium, platinum or rhodium on a suitable carrier such as carbon, barium sulfate, or alumina so that the cepham compound is not degraded. Preferred carboxy protecting groups include, for example, $C_4-C_6$ tertiary alkyl, 2,2,2-trihaloethyl, 2-iododethyl, benzyl, p-nitrobenzyl, succinimidomethyl, phthalimidomethyl, p-methoxybenzyl, benzhydryl, $C_2-C_6$ alkanoyloxymethyl, phenacyl, or p-halophenacyl, wherein in any of the above, halo denotes chlorine, bromime, or iodine.

Specific illustrations of the preferred ester residues of the carboxyl group of the 3-hydroxy-3-methylcepham compound used in the process of this invention include, for example, tert-butyl, 2,2,2-trichloroethyl, 2,2,2-tribromoethyl, 2-iodoethyl, benzyl, p-nitrobenzyl, succinimidomethyl, phthalimidomethyl, p-methoxybenzyl, benzhydryl, acetoxymethyl, pivaloyloxymethyl, phenacyl, p-clorophenacyl, p-bromophenacyl and the like.

Highly preferred ester residues are benzyl, p-nitrobenzyl, p-methoxybenzyl, benzhydryl, and 2,2,2-trichloroethyl. The most preferred ester residue is p-nitrobenzyl.

In the above formula as well as in that depicting the product of the process of this invention, R represents an acyl group such as $C_2$-$C_8$ alkanoyl, benzoyl, or a group represented by the formula P—(O)$_n$—(CH$_2$)$_m$C(O)— — wherein P is 2-thienyl, 3-thienyl, 2-furyl, 3-furyl, phenyl or phenyl substituted by $C_1$-$C_3$ alkyl, $C_1$-$C_3$ alkoxy, nitro, fluoro, chloro, bromo, iodo, cyano, or trifluoromethyl; n is 0 or 1, and m is 0 or an integer from 1 to 3 inclusive with the limitation that when n is 1, m is not 0, and P is phenyl or phenyl substituted by $C_1$-$C_3$ alkyl, $C_1$-$C_3$ alkoxy, nitro, fluoro, chloro, bromo, iodo, cyano, or trifluoromethyl.

Representative examples of the acyl groups represented by R include 2-thienylacetyl, 2-furylacetyl, 3-thienylacetyl, phenylacetyl, phenoxyacetyl, acetyl, pivaloyl, N-heptanolyl, phenylpropionyl, 3-ethylphenylbutanoyl 4-chlorophenylacetyl, 4-cyanophenylacetyl, 3-chlorophenylacetyl, 4-iso-propylphenylacetyl, 4-chlorophenylacetyl, 4-bromophenylacetyl, 4-nitrophenylacetyl, 3-cyanophenylacetyl, 3-ethoxyphenylacetyl, 4-iso-propoxyphenylpropionyl, 4-trifluoromethylphenoxyacetyl, and the like. Preferred acyl groups are phenylacetyl and phenoxyacetyl.

7-Acylamino-3-hydroxy-3-methylcepham-4-carboxylic acid esters described hereinabove but not mentioned specifically in U.S. Pat. No. 3,668,201 can be prepared from the 7-amino-3-hydroxy-3-methylcepham-4-carboxylic acid described therein, by acylation with the appropriate acid chloride, such as, 2-thienylacetyl chloride followed by esterification with the appropriate reagent. Acylation and esterification procedures are well known to those skilled in the art.

The following are representative of the product conversions which are available in accordance with the process of this invention. It will be understood, however, that the yield of products may vary depending upon the particular reactants which are employed, the relative quantities of reactants, and the conditions of the reaction.

Methyl 7-phenylacetamido-3-hydroxy-3-methylcepham-4-carboxylate to methyl 6-phenylacetamido-2α-methyl-2β-halomethylpenam-3-carboxylate which rearranges over a period of time to methyl 7-phenylacetamido-3β-halo-3α-methylcepham-4-carboxylate.

p-Nitrobenzyl 7-phenoxyacetamido-3-hydroxy-3-methylcepham-4carboxylate to p-nitrobenzyl 6-phenoxyacetamido-2α-methyl-2β-halomethylpenam-3-carboxylate which rearranges over a period of time to p-nitrobenzyl 7-phenoxyacetamido-3β-halo-3α-methylcepham-4-carboxylate.

Succinimidomethyl 7-(4-chlorophenylpropionamido)-3-hydroxy-3-methylcepham-4-carboxylate to succinimidomethyl 6-(4-chlorophenylpropionamido)-2α-methyl-2β-halomethylpenam-3-carboxylate which rearranges over a period of time to succinimidomethyl 7-(4-chlorophenylproprionamido)-3β-halo-3α-methylcepham-4-carboxylate.

Phthalimidomethyl 7-benzamido-3-hydroxy-3-methylcepham-4-carboxylate to phthalimido 6-benzamido-2α-methyl-2β-halomethylpenam-3-carboxylate which rearranges over a period of time to phthalimidomethyl 7-benzamido-3β-halo-3α-methylcepham-4-carboxylate.

2'-Iodoethyl, 7-acetamido-3-hydroxy-3-methylcepham-4-carboxylate to 2'-iodoethyl 6-acetamido-2α-methyl-2β-halomethylpenam-3-carboxylate which rearranges over a period of time to 2'-iodoethyl 7-acetamido-3β-halo-3α-methylcepham-4-carboxylate.

p-Nitrobenzyl 7-phenylacetamido-3-hydroxy-3-methylcepham-4-carboxylate to p-nitrobenzyl 6-phenylacetamido-2α-methyl-2β-halomethylpenam-3-carboxylate which rearrange over a period of time to p-nitrobenzyl 7-phenylacetamido-3β-halo-3α-methylcepham-4-carboxylate.

p-Methoxybenzyl 7-phenoxyacetamido-3-hydroxy-3-methylcepham-4-carboxylate to p-methoxybenzyl 6-phenoxyacetamido-2α-methyl-2β-halomethylpenam-3-carboxylate which rearranges over a period of time to p-methoxybenzyl 7-phenoxyacetamido-3β-halo-3α-methylcepham-4-carboxylate.

t-Butyl 7-(4-fluorophenylacetamido)-3-hydroxy-3-methylcepham-4-carboxylate to t-butyl 6-(4-fluorophenylacetamido)-2α-methyl-2β-halomethylpenam-3-carboxylate which rearranges over a period of time to to t-butyl 7-(4-fluorophenylacetamido)-3β-halo-3α-methylcepham-4-carboxylate.

p-Nitrobenzyl 7-(4-trifluoromethylphenoxyacetamido)-3-hydroxy-3-methylcepham-4-carboxylate to p-nitrobenzyl 6-(4-trifluoromethylphenoxyacetamido)-2α-methyl-2β-halomethylpenam-3-carboxylate which rearranges over a period of time to p-nitrobenzyl 7-(4-trifluoromethylphenoxyacetamido)-3β-halo-3α-methylcepham-4-carboxylate.

In the above representative conversions, the term "halo" refers to chloro or bromo. Whether the products are the chloro or the bromo derivatives is determined by the identity of the particular halogenating agent employed in the process.

The products produced in accordance with the process of this invention can be isolated and purified by employing conventional methods. These can include, for example, chromatographic separation, filtration, recrystallization, and the like.

The product 6-acylamino-2α-methyl-2β-halomethylpenam-3-carboxylic acid esters can be converted directly to a desacetoxycephalorporin compound of the formula

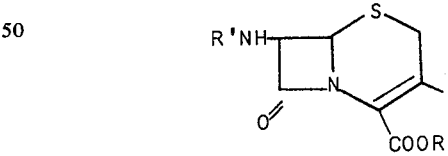

by treatment with 1 to 5 equivalents of a silver salt, e.g., silver nitrate, silver acetate or silver methanesulfonate in a solvent inert to the reactants such as acetone acetonitrile, or glacial acetic acid. The 2α-methyl-2β-bromomethyl penams can be converted to cephem compounds by dissolution in pyridine at room temperature for 2 hours.

Alternatively, the product penam compounds of the process of this invention can be allowed to rearrange as described hereinabove to the corresponding 3β-halo-3α-methylcephams which are converted to desacetoxycephalosporins by treatment with an organic base, e.g.

pyridine or triethylamine, or by treatment with a silver salt in an inert organic solvent.

The 7-acylamino-3-methyl-3-cepham-4-carboxylic acid ester thereby produced can be converted by known techniques to an active antibiotic by cleavage of the ester function. Deesterification can be achieved by treatment of the ester with an acid such as trifluoroeacetic acid, hydrochloric acid, and the like, or with zinc and an acid, such as formic acid, acetic acid, or hydrochloric acid. It can likewise be accomplished by hydrogenating the ester in the presence of palladium, platinum, rhodium, or a compound thereof, in suspension, or on a carrier such as barium sulfate, carbon, alumina or the like. The antibiotic activity of the resulting acids has been well documented.

The following examples are provided to further illustrate this invention. It is not intended that this invention be limited in scope by reason of any of these examples.

EXAMPLE 1

4'-nitrobenzyl 6-phenoxyacetamido-2α-methyl-2β-chloromethylpenam-3-carboxylate

A solution of 4'-nitrobenzyl 7-phenoxyacetamido-3-hydroxy-3-methylcepham-4-carboxylate (1.5 g., 3 mmol.), thionyl chloride (0.45 ml., 5.5 mmol.), and 2 ml. dimethylformamide in 180 ml. of dry benzene is heated to reflux under anhydrous conditions for 30 minutes. The mixture is cooled and evaporated in vacuo to dryness. The resulting red oil is dissolved in 120 ml. ethyl acetate and washed with water (2 × 100 ml.) and brine (100 ml), dried ($Na_2SO_4$) and evaporated in vacuo to give a dark foam. The crude product is chromatographed on an acid washed silica gel column (24 × 3 cm) developed with 7% ethyl acetate in benzene (20 ml. fractions).

Evaporation in vacuo of fractions 61-79 gives 400 mg. of an amorphous solid identified as 4'-nitrobenzyl 6-phenoxyacetamido-2α-methyl-2β-chloromethylpenam-3-carboxylate: nmr ($CDCl_3$) 91 (s, 3, 2-$CH_3$), 210 (s, 3, $C_2$-$CH_2Cl$), 274 (s, 2, side chain $CH_2$), 303 (s, 1, $C_3$-H), 320 (s, 2, ester $CH_2$), 340 (m, 2, azetidinone protons), and 410-500 Hz (m, 9, ArH); ir ($CHCl_3$) 1798 (azetidinone C=O), 1760 (ester C=O) and 1700 $cm^{-1}$ (amide C=O).

Anal. Calcd for $C_{23}H_{22}N_3O_7S$ Cl: C, 53.13; H, 4.26; N, 8.08; Cl, 6.82. Found: C, 53.34; H, 4.33; N, 8.26; Cl, 7.15.

Evaporation in vacuo of fractions 80–110 gives 270 mg. of a violet amorphous solid. The nmr spectrum of this solid showed it to be ca. 60% 4'-nitrobenzyl 6-phenoxyacetamido-2α-methyl-2β-chloromethylpenam-3-carboxylate.

The 2β-chloromethylpenam rearranges in the solid state (amorphous) over a 6 month period to the corresponding 4'-nitrobenzyl 7-phenoxyacetamido-3-chloro-3-methylcepham-4-carboxylate: nmr ($CDCl_3$) 100 (s, 3, $C_3$—$CH_3$), 165 and 220 (ABq, 2, J = 14 Hz, $C_2$—H), 290 (s, 1, $C_4$—H), 324, (d, 1, J = 4.5, $C_6$—H) and 345 Hz(q, 1, J = 4.5 and 8.0 Hz, $C_7$—H).

The β-chlorocepham product is converted quantatively to 4'-nitrobenzyl-7-phenoxyacetamido-3-methyl-3-cephem-4-carboxylate by its reaction with 1 equivalent of triethylamine in chloroform at room temperature.

EXAMPLE 2

2',2',2'-Trichloroethyl 6-phenylacetamido-2α-methyl-2β-bromo methylpenam-3-carboxylate.

2',2',2'-Trichloroethyl 7-phenylacetamido-3-hydroxy-3-methylcepham-4-carboxylate is added to a mixture of 1.1 equivalents of $PBr_5$ and dimethylformamide (about 5 equivalents) in dry benzene. The resulting mixture is refluxed for about 10 minutes, cooled and evaporated in vacuo to dryness. The resulting product mixture is taken up in ethyl acetate, washed with 1N. HCl and brine, and dried over magnesium sulfate. Evaporation in vacuo to dryness, followed by chromatography over silica gel gives 2',2',2'-trichloroethyl 6-phenylacetamido-2α-methyl-2β-bromomethylpenam-3-carboxylate.

EXAMPLE 3

4'-Nitrobenzyl 6-phenoxyacetamido-2α-methyl-2β-bromomethypenam-3-carboxylate.

4'-Nitrobenzyl 7-phenoxyacetamdo-3-hydroxy-3-methylcepham-4-carboxylate is added at room temperature to a solution of an equivalent amount of phosphorous pentabromide in dry dimethylacetamide. After 30 minutes at resulting temperature the reaction mixture is heated to 80°C. for about 10 minutes, cooled and poured into cold 5% sodium bicarbonate solution. The resulting solution is extracted with ethyl acetate. The organic extracts are combined, washed with 1N.HCl and brine, and dried over magnesium sulfate. Evaporation in vacuo gives 4'-nitrobenzyl 6-phenoxyacetamido-2α-methyl-2β-bromomethylpenam-3-carboxylate.

EXAMPLE 4

Benzhydryl 6-phenylacetamido-2α-methyl-2β-chloromethylpenam-3-carboxylate

The procedure of Example 2 is repeated except that benzhydryl 7-phenylacetamido-3-hydroxy-3-methylcepham-4-carboxylate is used as the starting material in place of the corresponding trichloroethyl ester and $PCl_5$ used in place of $PBr_5$. There is obtained as product the benzhydryl 6-phenylacetamido-2α-methyl-2β-chloromethylpenam-3-carboxylate.

EXAMPLE 5

4'-Methoxybenzyl 6-phenoxyacetamido-2α-methyl-2β-chloromethylpenam-3-carboxylate.

The procedure of Example 1 is repeated except that 4-methoxybenzyl 7-phenoxyacetamido-3-hydroxy-3-methylcepham-4-carboxylate is used as the starting material in place of the corresponding 4-nitrobenzyl ester and dimethylacetamide is used in place of the dimethylformamide. There is produced as product the 4'-methoxybenzyl 6-phenoxyacetamido-2α-methyl-2β-chloromethylpenam-3-carboxylate.

EXAMPLE 6

2',2',2'-Trichloroethyl 6-phenylacetamido-2α-methyl-2β-chloromethylpenam-3-carboxylate.

2',2',2'-trichloroethyl 7-phenylacetamido-3-hydroxy-3-methylcepham-4-carboxylate is added to a solution of 1.5 equivalents of thionyl chloride in anhydrous dimethylacetamide at room temperature. After stirring the mixture at room temperature for about 30 minutes, it is heated to 80°–90°C. for 10 minutes, cooled and poured slowly into a cold 5% sodium bicarbonate solution. The resulting aqueous solution is extracted with ethyl acetate. The organic extracts are combined, washed with 1N.HCl and brine and dried over magnesium sulfate. Evaporation in vacuo of the ethyl acetate solution gives 2',2',2'-trichloroethyl 6-phenylacetamido-2α-methyl-2β-chloromethylpenam-3-carboxylate which is purified by column chromatography over silica gel.

EXAMPLE 7

4'-Nitrobenzyl 6-phenoxyacetamido-2α-methyl-2β-chloromethylpenam-3-carboxylate was prepared in accordance with the general experimental procedure defined in Example 6 with the exceptions that phosgene (2-fold excess) was used as the halogenating agent in place of thionyl chloride and dry dimethylformamide (dried over 4A molecular sieves) was used as the solvent.

EXAMPLE 8

This example illustrates the conversion of the product compounds of this invention to the corresponding 3-methyl-3-cephem compounds via their reaction with silver salts.

Silver acetate (200 mg.) was added to a solution of 4'-nitrobenzyl 6-phenoxyacetamido-2α-methyl-2β-chloromethylpenam-3-carboxylate (400 mg.) in 10 ml. glacial acetic acid. The mixture was heated on a steam bath for 15 minutes, cooled, and evaporated in vacuo to near dryness. The crude product was taken up in 20 ml. ethyl acetate; the inorganic salts were filtered and the filtrate was evaporated to dryness. Comparative thin-layer chromatography indicated 3 products, two of which had r.f. values corresponding to those of 4'-nitrobenzyl 7-phenoxyacetamido-3-methyl-3-cephem-4-carboxylate and 4'-nitrobenzyl 7-phenoxyacetamido-3-acetoxy-3-methylcepham-4-carboxylate. Separation of the mixture by peparative thin-layer chromatography gave the following:

4'-nitrobenzyl 7-phenoxyacetamido-3-methyl-3-cephem-4-carboxylate (58 mg., 17%); nmr (CDCl$_3$) 131 (s, 3, CH$_3$), 197 and 215 (ABg, J=18Hz), 275 (s, 2, side-chain CH$_2$), 302 (d, 1, J=4.0Hz), 322 (s, 2, ester CH$_2$), 353 (q, 1, J=4.0Hz and J= 9.0 Hz) and 410–500 Hz (m, 9, ArH).

4'-nitrobenzyl 7-phenoxyacetamido-3-acetoxy-3-methylcepham-4-carboxylate (60 mg., 16%); nmr (CDCl$_3$) 92 (s, 3, 3-CH$_3$), 120 (s, 3, 3-OCOC$\underline{H}_3$), 203 (s, 2, C$_2$—H), 274 (s, 2 side chain C$\underline{H}_2$), 204 (s, 1, C$_4$—H), 318 (s, 2, ester CH$_2$), 320 (d, 1 J=4.0Hz, azetidinone H), 340 (q, 1, J=4.0 and J= 10.0 Hz) and 410–500 Hz (m, 9, ArH). This compound is identical to that prepared by method of Gutowski et. al. *Tetrahedron Letters*, No. 37, pp. 3429–3432 (1971).

The other product is isolated as a mixture with 4'-nitrobenzyl 7-phenoxyacetamido-3-methyl-3-cephem-4-carboxylate and is identified as 4'-nitrobenzyl 6-phenoxyacetamido-2-acetoxymethyl-2-methylpenam-3-carboxylate: nmr (CDCl$_3$), 85 (s, 3, C$_2$—C$\underline{H}_3$), 124 (s, 3, OCOCH$_3$), 228 and 260 (ABq, 2, J=11.0 Hz), 274 (s, 2, side chain CH$_2$), 285 (s, 1, C$_3$—H), 320 (s, 2, ester CH$_2$), 342 (m, 2, azetidinone H) and 410–500 Hz (m, 9, ArH).

EXAMPLE 9

4'-Nitrobenzyl 7-phenoxyacetamido-3-methyl-3-cephem-4-carboxylate

4'-Nitrobenzyl 6-phenoxyacetamido-2α-methyl-2β-bromomethylpenam-3-carboxylate is dissolved in pyridine and the resulting solution is stirred at room temperature for 2 hours. The reaction mixture is evaporated in vacuo to dryness. The product is then taken up in ethyl acetate and washed successively with 1N.HCl (2X), water, and brine and dried (Na$_2$SO$_4$). Evaporation in vacuo to dryness provides 4'-nitrobenzyl 7-phenoxyacetamido-3-methyl-3-cephem-4-carboxylate in high yield.

We claim:

1. The process of preparing a compound of the formula

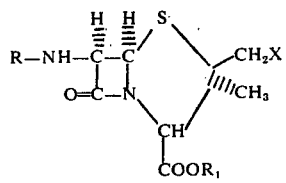

by reacting a 3-hydroxy-3-methylcepham compound of the formula

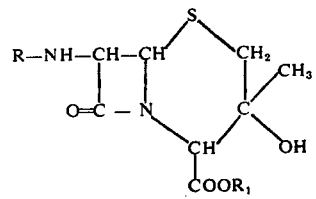

and at least 1 molar equivalent of a halogenating agent selected from the group consisting of CO(X)$_2$, SO(X)$_2$, and P(X)$_5$ in the presence of at least 1 molar equivalent (with respect to the halogenating agent) of a tertiary carboxamide selected from the group consisting of

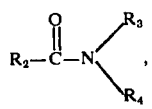

and

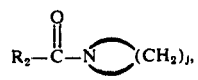

and

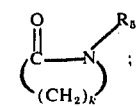

at a temperature between about 50° and 120°C., wherein in the above formulae, R is $C_2$–$C_8$ alkanoyl, benzoyl or a group represented by the formula $$P-(O)_n-(CH_2)_m C(O)--$$

wherein P is 2-thienyl, 3-thienyl, 2furyl, phenyl or phenyl substituted by $C_1$–$C_3$ alkyl, $C_1$–$C_3$ alkoxy, nitro, fluoro, chloro, bromo, iodo, cyano, or trifluoromethyl; $n$ is 0 or 1, and $m$ is 0, 1, 2, or 3; with the limitation that when $n$ is 1, $m$ is not 0, and P is phenyl or phenyl substituted by $C_1$–$C_3$ alkyl, $C_1$–$C_3$ alkoxy, nitro, fluoro, chloro, bromo, iodo, cyano, or trifluoromethyl;
$R_1$ is a conventional carboxylic acid protecting group; $R_2$ is hydrogen or $C_1$–$C_6$ alkyl, and each of $R_3$ and $R_4$ is independently $C_1$–$C_6$ alkyl, phenyl, tolyl or xylyl such that $R_3$ and $R_4$ together contain no more than 11 carbon atoms; $R_5$ is $C_1$–$C_6$ alkyl, phenyl, tolyl, or xylyl; $j$ an integer from 3 to 6 inclusive; $k$ is an integer from 3 to 6 inclusive; and X is chlorine or bromine.

2. The process of claim 1 wherein $R_1$ is 2,2,2-trihaloethyl, benzhydryl, $C_4$–$C_6$ tertiary alkyl, benzyl, methoxybenzyl, nitrobenzyl, $C_2$–$C_6$ alkanoyloxymethyl, phenacyl, succinimidoethyl, and phthalimidomethyl.

3. The process of claim 2 wherein $m$ is 1 and P is phenyl or phenyl substituted by $C_1$–$C_3$ alkyl, $C_1$–$C_3$ alkoxy nitro, fluoro, chloro, bromo, iodo, cyano, or trifluoromethyl.

4. The process of claim 3 wherein X is chlorine.

5. The process of claim 4 wherein the tertiary carboxamide is N,N-dimethylformamide, N,N-dimethylacetamide, or N-methyl-2-pyrrolidinone.

6. The process of claim 5 wherein the halogenating agent is thionyl chloride or phosphorous pentachloride.

7. The process of claim 6 wherein $R_1$ is benzyl, p-nitrobenzyl, p-methoxybenzyl, benzhydryl, or trichloroethyl.

8. The process of claim 7 wherein the 3-hydroxy-3-methylcepham compound is reacted with 1.1–2.0 equivalents of thionyl chloride and the tertiary carboxamide, present in an amount at least equivalent to the amount of thionyl chloride employed therein, at 50° to 90°C. in an aprotic solvent.

9. The process of claim 8 wherein P is phenyl and $m$ is 1.

10. The process of claim 9 wherein the aprotic solvent is benzene or toluene.

11. The process of claim 10 wherein the 3-hydroxy-3-methylcepham compound is p-nitrobenzyl 7-phenoxyacetamido-3-hydroxy-3-methylcepham-4-carboxylate.

12. The process of claim 5 wherein the 3-hydroxy-3-methylcepham compound is reacted with 1.1 to 2.0 equivalents of the halogenating agent in a tertiary carboxamide solvent at a temperature of about 60° to 90°C.

13. The process of claim 12 wherein P is phenyl and $m$ is 1.

* * * * *